(12) United States Patent
Izui et al.

(10) Patent No.: US 6,893,852 B1
(45) Date of Patent: May 17, 2005

(54) DNA ENCODING SUCROSE PTS ENZYME II

(75) Inventors: Masako Izui, Kawasaki (JP);
Masakazu Sugimoto, Kawasaki (JP);
Tsuyoshi Nakamatsu, Kawasaki (JP);
Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 151 days.

(21) Appl. No.: 10/019,284

(22) PCT Filed: Jun. 30, 2000

(86) PCT No.: PCT/JP00/04348

§ 371 (c)(1),
(2), (4) Date: Jan. 2, 2002

(87) PCT Pub. No.: WO01/02584

PCT Pub. Date: Jan. 11, 2001

(30) Foreign Application Priority Data

Jul. 2, 1999 (JP) .......................................... 11-189512

(51) Int. Cl.⁷ ............................. C12N 9/12; C07H 21/04
(52) U.S. Cl. ...................................... 435/194; 536/23.2
(58) Field of Search ................................ 435/194, 193; 536/23.2, 23.7; 530/350

(56) References Cited

U.S. PATENT DOCUMENTS

| | | |
|---|---|---|
| 5,556,776 A | 9/1996 | Tsuchiya et al. ............ 435/106 |
| 5,616,480 A | 4/1997 | Sugimoto et al. |
| 5,688,671 A | 11/1997 | Sugimoto et al. |
| 5,756,347 A | 5/1998 | Sugimoto et al. |
| 5,766,925 A | 6/1998 | Sugimoto et al. |
| 5,804,414 A | 9/1998 | Moriya et al. |
| 5,876,983 A | 3/1999 | Sugimoto et al. |
| 5,919,694 A | 7/1999 | Sugimoto et al. |
| 6,004,773 A | 12/1999 | Araki et al. |
| 6,037,154 A | 3/2000 | Suga et al. |
| 6,090,597 A | 7/2000 | Hirano et al. |
| 6,221,636 B1 | 4/2001 | Hayakawa et al. |
| 6,258,573 B1 | 7/2001 | Suga et al. |
| 6,395,528 B1 | 5/2002 | Suga et al. |
| 6,696,561 B1 | 2/2004 | Pompejus et al. ......... 536/23.7 |
| 2002/0197605 A1 | 12/2002 | Nakagawa et al. ............ 435/6 |
| 2004/0030116 A1 | 2/2004 | Pompejus et al. ......... 536/23.7 |

FOREIGN PATENT DOCUMENTS

| | | |
|---|---|---|
| EP | 724017 | 9/1997 |
| EP | 1 108 790 | 6/2001 |
| JP | 5-244958 | 9/1993 |
| JP | 8-196280 | 8/1996 |
| WO | WO01/00802 | 1/2001 |
| WO | WO01/00804 | 1/2001 |
| WO | WO01/00805 | 1/2001 |
| WO | WO01/00842 | 1/2001 |
| WO | WO01/00843 | 1/2001 |
| WO | WO01/00844 | 1/2001 |
| WO | WO01/00845 | 1/2001 |
| WO | WO 01/02583 | 1/2001 |

OTHER PUBLICATIONS

K. J. Leenhouts, et al., Database EMBL Online I, Pediococcus Pentosaceus Reffinose Operon Genes, Database Accession No. L32093, pp. 1–8, XP–002240257, "The Sucrose and Raffinose Operons of Pediococcus Pentosaceus PPE1.0", May 3, 1994.

J.–K. Lee, et al., FEMS MIcrobiology Letters, vol. 119, No. 1–2, pp. 137–145, XP–000960685. "Nucleotide Sequence of the Gene Encoding the Cortynebacterium Glutamicum Mannose Enzyme II and Analyses of the Deduced Protein Sequence", 1994.

H. Dominiquez, et al., Applied and Environmental Microbiology, vol. 62, No. 10, pp. 3878–3880, XP–000960659, "Complete Sucrose Metabolism Requires Fructose Phosphotransferase Actitivity in Corynebacterium Glutamicum to Ensure Phosphorylation of Liberated Fructose", Oct. 1996.

Y. Kawahara, et al., Applied Microbiology and Biotechnology, vol. 34, No. 3, pp. 340–343, XP–000571746, "Effect of Glycine Betaine on the Sucrose Catabolism of An L–Lysine Producing Mutant of Brevibacterium Lactofermentum", Dec. 1, 1990.

J. F. Martin, et al., Bio/Technology, vol. 5, pp. 137–146, XP–002034056, "Cloning Systemes in Amino Acid–Producing Corynebacteria". Feb. 1, 1987.

P. Gunasekaran et al.: "Cloning and sequencing of the sacA gene: characterization (sucrase from Zymomonas mobilis)" J. Bacteriol. vol. 172, No. 12, pp. 6727–2735 1990.

J. Reizer et al.: "Novel phosphortransferase system revealed by bacterial genome analysis—a gene cluster encoding a unique Enzyme I and the proteins of a fructose–like permease system." Microbiology, vol. 141, pt. 4, pp. 961–971 1995.

UF Wehmeier et al.: "Molecular analysis of the phosphoenolpyruvate–dependent L–sorbose: phosphotransferase system from Klebaiella pneumoniae and of its multidomain structure" Mol. Gen.Genet., vol. 246, No. 5, pp. 610–618, 1995.

Steffan Tobisch et al.: "Identification and characterization of a new B–glucoside utilization system in Bacillus subtils" Journal of Bacteriology, vol. 179, No. 2, pp. 496–506, 1997.

(Continued)

*Primary Examiner*—Elizabeth Slobodyansky
(74) *Attorney, Agent, or Firm*—Shelly Guest Cermak

(57) ABSTRACT

A gene encoding a protein constituting sucrose PTS of coryneform bacterium is provided by amplifying a region existing downstream from sucrase gene in coryneform bacterium by the cassette-ligation mediated PCR to obtain DNA encoding sucrose PTS enzyme II, which is a protein defined in the following (A) or (B):

(A) a protein which has the amino acid sequence of SEQ ID NO: 2 in Sequence Listing;

(B) a protein which has the amino acid sequence of SEQ ID NO: 2 in Sequence Listing including substitution, deletion, insertion, addition or inversion of one or several amino acids, and an activity for binding to sucrose.

5 Claims, 2 Drawing Sheets

OTHER PUBLICATIONS

Y. Sato et al.: "Characterization and sequency analysis of the scrA gene encoding enzyme II Scr of the Steptococcus Posphotransferas system" J. Bacteriol, vol. 171, No. 1, pp. 263–271, 1989.

E. Wagner et al.: "Cloning and characterization of the ScrA gene encoding the sucrose–specific Enzyme II of the phosphotransferase system from Staphylococcus xylosus" Mol. Gen.Genet., vol. 241, No. 1–2, pp. 33–41, 1993.

H. De Reuse, et al., Journal of Bacteriology, vol. 170, No. 9, pp. 3827–3837, "The ptsH, ptsl, and crr Genes of the *Escherichia coli* Phosphoenolpyruvate–Dependent Phosphotransferase System: A Complex Operon with Several Modes of Transcription", Sep. 1988.

B. Erni, et al., The Journal of Biological Chemistry, vol. 261, No. 35, pp. 16398–16403, "Glucose–Permease of the Bacterial Phosphotransferase System", 1986.

S. O. Nelson, et al., The EMBO Journal, vol. 3, No. 7, pp. 1587–1593, "Molecular Cloning, Sequencing, and Expression of the crr Gene: The Structural Gene for III$^{Glc}$ of the Bacterial Pep: Glucose Phosphotransferase System", 1984.

D. W. Saffen, et al., The Journal of Biological Chemistry, vol. 262, No. 33, pp. 16241–16253, "Sugar Transport by The Bacterial Phosphotransferase System", Nov. 25, 1987.

U.S. Appl. No. 09/648,482, filed Aug. 28, 2000, Suga et al.

U. S. Appl. No. 09/936,181, filed Sep. 10, 2001, Araki, et al.

U. S. Appl. No. 10/009,777, filed Dec. 17, 2001, Sugimoto, et al.

U. S. Appl. No. 10/148,898, filed Jun. 19, 2002, Sugimoto, et al.

U. S. Appl. No. 10/195,548, filed Jul. 16, 2002, Suga et al.

U. S. Appl. No. 10/226,136, filed Aug. 23, 2002, Otsuna et al.

U. S. Appl. No. 10/307,320, filed Dec. 2, 2002, Hibino et al.

U. S. Appl. No. 10/321,382, filed Dec. 18, 2002, Suga et al.

U. S. Appl. No. 10/320,647, filed Dec. 17, 2002, Suga et al.

Office Action issued from Australian Patent Office in application No. 55713/00 on Sep. 30, 2004.

SEQUENCE LISTING

<160> NUMBER OF SEQ ID NOS: 21

<210> SEQ ID NO 1
<211> LENGTH: 5969
<212> TYPE: DNA
<213> ORGANISM: Brevibacterium lactofermentum
<220> FEATURE:
<221> NAME/KEY: CDS
<222> LOCATION: (3779)..(5761)
<223> OTHER INFORMATION:

<400> SEQUENCE: 1

```
agtccgtcga cgccaccatt gatgtggtgg tcaccgagct tgcggaggct ttctacatct      60
acgctcccgt cggcgtggag tggggtcatt acgggtggga tcacgccggt gaaagttgcg     120
gaacccatgg tgttccttgt gggttgaggg aacgagtgcg ggtgagaagt ttttcaagtg     180
tctgcagttt ttaagttatg catcatcagc ttggaaggct gaggtaattc agtagacctg     240
caacagcagg cctcaagtcc gaagataatt aacctagatc cgtagacata agacatcata     300
cgtcctatgc ttgctggaag gaaccaaata acctcagaaa gatggcagaa gtggtgcatt     360
atcaagaaaa tgcaggtcaa gcagttaaaa aaattgaggg aagaattgtt cccccctcg      420
gggtgattga tggctttctc caactcgaaa acggcatcat cacggaactc tctggagaac     480
cagcacctaa aaacgcagga ttccaccccg aactccccac gattgttccc ggttttattg     540
atcttcataa tcacggtgga aacggtggcg cgtttcctac gggaacgcag gaccaggcga     600
ggaacaccgc gcagtatcac cgcgaacatg gcacgaccgt gatgttgcca agcatggttt     660
cggcgccggc tgacgcactg gcagcgcagg tggaaaacct tattcccttg tgtgaagagg     720
tcctgctgtg cggcattcac ctcgagggcc ctttcatcaa cgcatgccgt tgtggtgctc     780
aaaacccgga tttcattttt cccggcaacc aacagatct tgcccgggtg atccatgcgg      840
gaaaaggttg gatcaaatcg atcacagtag cgccggaaac tgacaatctt tctgagcttc     900
tcgatcctg cgcagcgcac cacatcattg cttccttcgg gcacactgat gcagattttg      960
ataccactac cagcgcaatt gccttggcta agagaaaaa tgtgacggtc acggctacgc    1020
atttgttcaa tgcgatgcct ccgctgcatc atagggctcc cggcagcgtg ggcgcttttgc    1080
ttgctgcggc acgtgccggg gacgcatatg ttgagttgat cgccgacggc gtgcatttgg    1140
ccgatggaac ggtcgatcta gctcgttcca caacgccctt tttcatcacg gacgccatgg    1200
aagccgccgg aatgccagac ggtgagtaca ttttgggcgt tttgaacgtc accgtcaccg    1260
atggagtcgc ccgtctgcgc gatggcggcg ccatcgccgg gggcaccagc acactagcga    1320
gtcagttcgt gcaccacgtg cgcagggta tgacgcttat cgacgcgacc ctccacacct    1380
caaccgtcgc cgctaaaatt ctcggtcttg gcgatcacga aatcgctaaa tccaaccctg    1440
caaattttgt ggtctttgac tcaaacggcc aggtgcaaaa ggtccattta ggtcatcaag    1500
tactttaagt acgagtaaaa ctatcctgat tttaaggag tcccaccatg gaaatcacta    1560
tctgcaaaga cgagcaagaa gtcggcaaag cagttcagt cctaatcgca cccttcgcca    1620
acaaggtgg aaccttgggg cttgcaacag gatcctcacc actgagtacc taccaagagc    1680
tcattcgcat gtatgaagct ggggaagtgt cattcaagaa ctgcaaggca ttcttgttgg    1740
atgaatacgt gggactaacc cgtgacgatg aaaacagcta cttttaaaacc attcgcaaag    1800
agttcactga ccacatcgac atcgttgatg aagaggtcta cagcccagat ggtgcaaacc    1860
ctgatccata cgaagcagct gcagagtatg aggcaaagat cgctgcagaa tccgttgaag    1920
```

```
ttcaaatcct tggcatcggc ggaaacggca catcgctttc attgaaccat catcttctct   1980
gtcaggactg acaaaggtcc aggcgctgca ccctaaaact gtggaggaca acgctcgatt   2040
cttcaacacc atcgaagagg tcccaaccca cgccgtcacc cagggtttgg cactttgtc    2100
ccgcgcgcaa acatcgtgt tggtggcaac tggtgaagga aaagccgacg ccatccgcgg    2160
aactgtggaa ggcccagtga ctgcttcttg cccaggttcc atcctgtaga tgcacaacat   2220
gccaccatca tcgttggatg aagcagcagt atccaagctg aaaacgctg atcactaccg    2280
tctcatggag caattaaagc tgcgctagaa acaaaaagga agtactgtg tggggctatg    2340
cacacagaac tttccagttt gcgccctgcg taccatgtga ctcctccgca gggcaggctc   2400
aatgatccca acggaatgta cgtcgatgga gatacccctcc acgtctacta ccagcacgat  2460
ccaggtttcc ccttcgcacc aaagcgcacc ggctgggctc acaccaccac gccgttgacc   2520
ggaccgcagc gattgcagtg gacgcacctg cccgacgctc tttacccgga tgcatcctat   2580
gacctggatg gatgctattc cggtggagcc gtatttactg acggcacact taaactttc    2640
tacaccggca acctaaaaat tgacggaaag cgccgcgcca cccaaaacct tgtcgaagtc   2700
gaggacccaa ctgggctgat gggcggcatt catcgccgtt cgcctaaaaa tccgcttatc   2760
gacggacccg ccagcggttt cacaccccat taccgcgatc ccatgatcag ccctgatggt   2820
gatggttgga acatggttct tggggcccaa cgcgaaaacc tcaccggtgc agcggttcta   2880
taccgctcga cagatcttga aaactgggaa ttctccggtg aaatcacctt tgacctcagt   2940
gatgcacaac ctggttctgc tcctgatctc gttcccgatg ctacatgtg gaatgcccc    3000
aacctttta cgcttcgcga tgaagaaact ggcgaagatc tcgacgtgct gattttctgt   3060
ccacaaggat tggaccgaat ccacgatgag gttactcact acgcaagctc tgaccagtgc   3120
ggatatgtcg tcgacaagct tgaaggaacg accttccgcg tcttgcgagg attcagcgag   3180
ctggatttcg gccatgaatt ctacgcaccg caggttgcag taaacggttc tgatgcctgg   3240
ctcgtgggct ggatggggct gcccgcgcag gatgatcacc caacagttgc acaggaagga   3300
tgggtgcact gcctgactgt gccccgcaag cttcatttgc gcaaccacgc gatctaccaa   3360
gagctccttc tcccagaggg ggagtcgggg gtaatcagat ctgtattagg ttctgaacct   3420
gtccgagtag acatccgagg caatatttcc ctcgagtggg atggtgtccg tttgtctgtg   3480
gatcgtgatg gtgatcgtcg cgtagctgag gtaaaacctg gcgaattagt gatcgcggac   3540
gataatacag ccattgagat aactgcaggt gatggacagg tttcattcgc ttttccgggc   3600
cttcaaaggt gacactattg agagataagt catataaaag ggtcttttgt ggcgaattgt   3660
acaaatactt cgcaaaatcc cttgatcgga cacaaataaa caggtttaat attgtttagc   3720
ttttgaacaa acattcatgt ctgaatattt ttgtttcttc ccggttaagg agaaaattc    3778
atg gac cat aag gac ctc gcg caa cgc atc ctg cgc gac att ggc ggc    3826
Met Asp His Lys Asp Leu Ala Gln Arg Ile Leu Arg Asp Ile Gly Gly
1               5                   10                  15
gaa gac aac att gtc gcc gcc gca cac tgt gca acg cgt tta cgc ctc    3874
Glu Asp Asn Ile Val Ala Ala Ala His Cys Ala Thr Arg Leu Arg Leu
            20                  25                  30
gtg ctc aaa gac acc aag gat gtg gat cgc caa agt ctg gat gat gat    3922
Val Leu Lys Asp Thr Lys Asp Val Asp Arg Gln Ser Leu Asp Asp Asp
        35                  40                  45
cca gat ctg aaa ggc acc ttt gaa act ggc ggc atg ttc cag atc atc    3970
Pro Asp Leu Lys Gly Thr Phe Glu Thr Gly Gly Met Phe Gln Ile Ile
    50                  55                  60
gtc ggg cca ggc gat gtg gat cat gtt ttc aaa gaa ctc gat gac gca    4018
```

-continued

```
Val Gly Pro Gly Asp Val Asp His Val Phe Lys Glu Leu Asp Asp Ala
65              70                  75                  80 acc tcc aaa gac atc gct gtg tcc aca gag cag ctc aaa gat gtt gtg   4066
Thr Ser Lys Asp Ile Ala Val Ser Thr Glu Gln Leu Lys Asp Val Val
            85                  90                  95 gct aac aac gcc aac tgg ttc agc cgt gct gtg aag gta ttg gcg gac   4114
Ala Asn Asn Ala Asn Trp Phe Ser Arg Ala Val Lys Val Leu Ala Asp
        100                 105                 110 att ttc gtc ccg ctg att cca atc ttg gtt ggt ggc ggt ctg ctc atg   4162
Ile Phe Val Pro Leu Ile Pro Ile Leu Val Gly Gly Gly Leu Leu Met
            115                 120                 125 gct atc aac aat gtg ttg gtt gcg cag gat ctg ttc ggt ccg caa tca   4210
Ala Ile Asn Asn Val Leu Val Ala Gln Asp Leu Phe Gly Pro Gln Ser
    130                 135                 140 ctg gtg gag atg ttc cct cag atc agc ggt gtt gct gag atg atc aac   4258
Leu Val Glu Met Phe Pro Gln Ile Ser Gly Val Ala Glu Met Ile Asn
145                 150                 155                 160 ctg atg gca tct gcg ccg ttc gcg ttc ttg cca gtg ttg gtt ggt ttc   4306
Leu Met Ala Ser Ala Pro Phe Ala Phe Leu Pro Val Leu Val Gly Phe
                165                 170                 175 acc gca acc aag cgt ttc ggt ggc aat gag ttc ctg ggc gcc ggc att   4354
Thr Ala Thr Lys Arg Phe Gly Gly Asn Glu Phe Leu Gly Ala Gly Ile
            180                 185                 190 ggt atg gcg atg gtg ttc cca acc ctg gtt aac ggc tac gac gtg gcc   4402
Gly Met Ala Met Val Phe Pro Thr Leu Val Asn Gly Tyr Asp Val Ala
        195                 200                 205 gcc acc atg acc gcg ggc gaa atg cca atg tgg tcc ctg ttt ggt ttg   4450
Ala Thr Met Thr Ala Gly Glu Met Pro Met Trp Ser Leu Phe Gly Leu
210                 215                 220 gat gtt gct caa gct ggt tac cag ggc acc gtg ctt cct gtg ctg gtg   4498
Asp Val Ala Gln Ala Gly Tyr Gln Gly Thr Val Leu Pro Val Leu Val
225                 230                 235                 240 gtc tct tgg att ctg gca acg atc gag aag ttc ctg cac aag cga ctc   4546
Val Ser Trp Ile Leu Ala Thr Ile Glu Lys Phe Leu His Lys Arg Leu
                245                 250                 255 atg ggc act gca gac ttc ctg atc acc cca gtg ttg act ctg ctg ctc   4594
Met Gly Thr Ala Asp Phe Leu Ile Thr Pro Val Leu Thr Leu Leu Leu
            260                 265                 270 acc ggc ttc ctt acg ttc att gct att ggt cca gca atg cgc tgg gtg   4642
Thr Gly Phe Leu Thr Phe Ile Ala Ile Gly Pro Ala Met Arg Trp Val
        275                 280                 285 ggt gac ttg ctg gca cac ggt ctg cag gga ctc tat gat ttc ggt ggt   4690
Gly Asp Leu Leu Ala His Gly Leu Gln Gly Leu Tyr Asp Phe Gly Gly
        290                 295                 300 cca gtc ggc ggt ctg ctt ttc ggt ctg gtc tac tca cca atc gtt atc   4738
Pro Val Gly Gly Leu Leu Phe Gly Leu Val Tyr Ser Pro Ile Val Ile
305                 310                 315                 320 act ggt ctg cac cag tcc ttc ccg cca att gag ctg gag ctg ttc aac   4786
Thr Gly Leu His Gln Ser Phe Pro Pro Ile Glu Leu Glu Leu Phe Asn
                325                 330                 335 cag ggt gga tcc ttc atc ttc gca acc gca tcc atg gcc aat atc gcg   4834
Gln Gly Gly Ser Phe Ile Phe Ala Thr Ala Ser Met Ala Asn Ile Ala
            340                 345                 350 cag ggt gca gca tgt ttg gca gtg ttc ttc cta gcg aag agt gaa aag   4882
Gln Gly Ala Ala Cys Leu Ala Val Phe Phe Leu Ala Lys Ser Glu Lys
        355                 360                 365 ctc aag ggc ctt gca ggt gct tca ggt gtc tcc gct gtt ctt ggt att   4930
Leu Lys Gly Leu Ala Gly Ala Ser Gly Val Ser Ala Val Leu Gly Ile
370                 375                 380
```

-continued

| | |
|---|---|
| aca gag cct gcg atc ttc ggt gtg aac ctt cgc ctg cgc tgg ccg ttc<br>Thr Glu Pro Ala Ile Phe Gly Val Asn Leu Arg Leu Arg Trp Pro Phe<br>385                            390                       395                    400 | 4978 |
| tac att ggt atc ggt acc gca gct atc ggt ggc gct ttg att gca ctc<br>Tyr Ile Gly Ile Gly Thr Ala Ala Ile Gly Gly Ala Leu Ile Ala Leu<br>                         405                       410                       415 | 5026 |
| ttt gat atc aag gca gtt gcg ttg ggc gct gca ggt ttc ttg ggt gtt<br>Phe Asp Ile Lys Ala Val Ala Leu Gly Ala Ala Gly Phe Leu Gly Val<br>              420                       425                       430 | 5074 |
| gtt tct att gat gct cca gat atg gtc atg ttc ttg gtt tgc gcg gta<br>Val Ser Ile Asp Ala Pro Asp Met Val Met Phe Leu Val Cys Ala Val<br>       435                       440                       445 | 5122 |
| gtt acc ttt gtc atc gca ttc ggc gca gcg att gct tat ggc ctt tac<br>Val Thr Phe Val Ile Ala Phe Gly Ala Ala Ile Ala Tyr Gly Leu Tyr<br>450                            455                       460 | 5170 |
| ttg gtt cgc cgc aac ggc agc att gat cca gat gca acc gct gct cca<br>Leu Val Arg Arg Asn Gly Ser Ile Asp Pro Asp Ala Thr Ala Ala Pro<br>465                            470                       475                    480 | 5218 |
| gtg cct gca gga acg acc aaa gcc gaa gca gaa gca ccc gca gaa ttt<br>Val Pro Ala Gly Thr Thr Lys Ala Glu Ala Glu Ala Pro Ala Glu Phe<br>                       485                       490                       495 | 5266 |
| tca aac gat tcc acc atc atc cag gca cct ttg acc ggt gaa gct atc<br>Ser Asn Asp Ser Thr Ile Ile Gln Ala Pro Leu Thr Gly Glu Ala Ile<br>              500                       505                       510 | 5314 |
| gca ctg agc agc gtc agc gat gcc atg ttt gcc agc gga aag ctt ggc<br>Ala Leu Ser Ser Val Ser Asp Ala Met Phe Ala Ser Gly Lys Leu Gly<br>       515                       520                       525 | 5362 |
| tca ggt gtt gcg atc gtc ccc acc aag ggg cag ctg gtt tca cca gtg<br>Ser Gly Val Ala Ile Val Pro Thr Lys Gly Gln Leu Val Ser Pro Val<br>530                            535                       540 | 5410 |
| agc gga aag atc gtg gtg gcc ttc cca tct ggt cac gct ttc gca gtc<br>Ser Gly Lys Ile Val Val Ala Phe Pro Ser Gly His Ala Phe Ala Val<br>545                            550                       555                    560 | 5458 |
| cgc act aag gct gag gat ggt tcc aat gtg gat atc ttg atg cac att<br>Arg Thr Lys Ala Glu Asp Gly Ser Asn Val Asp Ile Leu Met His Ile<br>                       565                       570                       575 | 5506 |
| ggt ttc gac acc gta aac ctc aac ggc acg cac ttt aac ccg ctg aag<br>Gly Phe Asp Thr Val Asn Leu Asn Gly Thr His Phe Asn Pro Leu Lys<br>              580                       585                       590 | 5554 |
| aag cag ggc gat gaa gtc aaa gca ggg gag ctg ctg tgt gaa ttc gat<br>Lys Gln Gly Asp Glu Val Lys Ala Gly Glu Leu Leu Cys Glu Phe Asp<br>       595                       600                       605 | 5602 |
| att gat gcc att aag gct gca ggt tat gag gta acc acg ccg att gtt<br>Ile Asp Ala Ile Lys Ala Ala Gly Tyr Glu Val Thr Thr Pro Ile Val<br>610                            615                       620 | 5650 |
| gtt tcg aat tac aag aaa acc gga cct gta aac act tac ggt ttg ggc<br>Val Ser Asn Tyr Lys Lys Thr Gly Pro Val Asn Thr Tyr Gly Leu Gly<br>625                            630                       635                    640 | 5698 |
| gaa att gaa gcg gga gcc aac ctg ctc aac gtc gca aag aaa gaa gcg<br>Glu Ile Glu Ala Gly Ala Asn Leu Leu Asn Val Ala Lys Lys Glu Ala<br>                       645                       650                       655 | 5746 |
| gtg cca gca aca cca taagttgaaa ccttgagtgt tcgcacacag gttagactag<br>Val Pro Ala Thr Pro<br>              660 | 5801 |
| gggacgtgac tctacgcatc tttgacaccg gtacccgtac gcttcgagat tttaaacctg | 5861 |
| ttcaaccagg tcatgcctcg gtgtacctgt gtggtgccac cccgcaatct tcaccccaca | 5921 |
| ttggacatgt tcgttcagca gtagcgtttg atattttgcg ccgctgaa | 5969 |

<210> SEQ ID NO 2
<211> LENGTH: 661
<212> TYPE: PRT
<213> ORGANISM: Brevibacterium lactofermentum

<400> SEQUENCE: 2

```
Met Asp His Lys Asp Leu Ala Gln Arg Ile Leu Arg Asp Ile Gly Gly
1               5                   10                  15

Glu Asp Asn Ile Val Ala Ala His Cys Ala Thr Arg Leu Arg Leu
                20                  25                  30

Val Leu Lys Asp Thr Lys Asp Val Asp Arg Gln Ser Leu Asp Asp Asp
                35                  40                  45

Pro Asp Leu Lys Gly Thr Phe Glu Thr Gly Gly Met Phe Gln Ile Ile
    50                  55                  60

Val Gly Pro Gly Asp Val Asp His Val Phe Lys Glu Leu Asp Asp Ala
65                  70                  75                  80

Thr Ser Lys Asp Ile Ala Val Ser Thr Glu Gln Leu Lys Asp Val Val
                85                  90                  95

Ala Asn Asn Ala Asn Trp Phe Ser Arg Ala Val Lys Val Leu Ala Asp
                100                 105                 110

Ile Phe Val Pro Leu Ile Pro Ile Leu Val Gly Gly Leu Leu Met
            115                 120                 125

Ala Ile Asn Asn Val Leu Val Ala Gln Asp Leu Phe Gly Pro Gln Ser
        130                 135                 140

Leu Val Glu Met Phe Pro Gln Ile Ser Gly Val Ala Glu Met Ile Asn
145                 150                 155                 160

Leu Met Ala Ser Ala Pro Phe Ala Phe Leu Pro Val Leu Val Gly Phe
                165                 170                 175

Thr Ala Thr Lys Arg Phe Gly Gly Asn Glu Phe Leu Gly Ala Gly Ile
                180                 185                 190

Gly Met Ala Met Val Phe Pro Thr Leu Val Asn Gly Tyr Asp Val Ala
        195                 200                 205

Ala Thr Met Thr Ala Gly Glu Met Pro Met Trp Ser Leu Phe Gly Leu
    210                 215                 220

Asp Val Ala Gln Ala Gly Tyr Gln Gly Thr Val Leu Pro Val Leu Val
225                 230                 235                 240

Val Ser Trp Ile Leu Ala Thr Ile Glu Lys Phe Leu His Lys Arg Leu
                245                 250                 255

Met Gly Thr Ala Asp Phe Leu Ile Thr Pro Val Leu Thr Leu Leu Leu
                260                 265                 270

Thr Gly Phe Leu Thr Phe Ile Ala Ile Gly Pro Ala Met Arg Trp Val
            275                 280                 285

Gly Asp Leu Leu Ala His Gly Leu Gln Gly Leu Tyr Asp Phe Gly Gly
    290                 295                 300

Pro Val Gly Gly Leu Leu Phe Gly Leu Val Tyr Ser Pro Ile Val Ile
305                 310                 315                 320

Thr Gly Leu His Gln Ser Phe Pro Pro Ile Glu Leu Glu Leu Phe Asn
                325                 330                 335

Gln Gly Gly Ser Phe Ile Phe Ala Thr Ala Ser Met Ala Asn Ile Ala
                340                 345                 350

Gln Gly Ala Ala Cys Leu Ala Val Phe Leu Ala Lys Ser Glu Lys
        355                 360                 365

Leu Lys Gly Leu Ala Gly Ala Ser Gly Val Ser Ala Val Leu Gly Ile
    370                 375                 380
```

-continued

```
Thr Glu Pro Ala Ile Phe Gly Val Asn Leu Arg Leu Arg Trp Pro Phe
385                 390                 395                 400

Tyr Ile Gly Ile Gly Thr Ala Ala Ile Gly Gly Ala Leu Ile Ala Leu
                405                 410                 415

Phe Asp Ile Lys Ala Val Ala Leu Gly Ala Ala Gly Phe Leu Gly Val
                420                 425                 430

Val Ser Ile Asp Ala Pro Asp Met Val Met Phe Leu Val Cys Ala Val
                435                 440                 445

Val Thr Phe Val Ile Ala Phe Gly Ala Ala Ile Ala Tyr Gly Leu Tyr
                450                 455                 460

Leu Val Arg Arg Asn Gly Ser Ile Asp Pro Asp Ala Thr Ala Ala Pro
465                 470                 475                 480

Val Pro Ala Gly Thr Thr Lys Ala Glu Ala Glu Ala Pro Ala Glu Phe
                485                 490                 495

Ser Asn Asp Ser Thr Ile Ile Gln Ala Pro Leu Thr Gly Glu Ala Ile
                500                 505                 510

Ala Leu Ser Ser Val Ser Asp Ala Met Phe Ala Ser Gly Lys Leu Gly
                515                 520                 525

Ser Gly Val Ala Ile Val Pro Thr Lys Gly Gln Leu Val Ser Pro Val
530                 535                 540

Ser Gly Lys Ile Val Ala Phe Pro Ser Gly His Ala Phe Ala Val
545                 550                 555                 560

Arg Thr Lys Ala Glu Asp Gly Ser Asn Val Asp Ile Leu Met His Ile
                565                 570                 575

Gly Phe Asp Thr Val Asn Leu Asn Gly Thr His Phe Asn Pro Leu Lys
                580                 585                 590

Lys Gln Gly Asp Glu Val Lys Ala Gly Glu Leu Leu Cys Glu Phe Asp
                595                 600                 605

Ile Asp Ala Ile Lys Ala Ala Gly Tyr Glu Val Thr Thr Pro Ile Val
                610                 615                 620

Val Ser Asn Tyr Lys Lys Thr Gly Pro Val Asn Thr Tyr Gly Leu Gly
625                 630                 635                 640

Glu Ile Glu Ala Gly Ala Asn Leu Leu Asn Val Ala Lys Lys Glu Ala
                645                 650                 655

Val Pro Ala Thr Pro
                660
```

<210> SEQ ID NO 3
<211> LENGTH: 44
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
gtacatattg tcgttagaac gcgtaatacg actcactata ggga                    44

<210> SEQ ID NO 4
<211> LENGTH: 47
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
gtacatattg tcgttagaac gcgtaatacg actcactata gggagag                 47

```
<210> SEQ ID NO 5
<211> LENGTH: 46
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
gtacatattg tcgttagaac gcgtaatacg actcactata gggaga          46

<210> SEQ ID NO 6
<211> LENGTH: 51
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gtacatattg tcgttagaac gcgtaatacg actcactata gggagactgc a    51

<210> SEQ ID NO 7
<211> LENGTH: 47
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
gtacatattg tcgttagaac gcgtaatacg actcactata gggagag         47

<210> SEQ ID NO 8
<211> LENGTH: 47
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
gtacatattg tcgttagaac gcgtaatacg actcactata gggagat         47

<210> SEQ ID NO 9
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cgtcttgcga ggattcagcg agctg                                 25

<210> SEQ ID NO 10
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
agctggattt cggccatgaa ttcta                                 25

<210> SEQ ID NO 11
<211> LENGTH: 23
<212> TYPE: DNA
<213> ORGANISM: ARTIFICIAL SEQUENCE
<220> FEATURE:
<223> OTHER INFORMATION: SYNTHETIC DNA
```

```
<400> SEQUENCE: 11
gatctgttcg gtccgcaatc act                                          23

<210> SEQ ID NO 12
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
cactggtgga gatgttccct cagat                                        25

<210> SEQ ID NO 13
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
catcttcgca accgcatcca tggcc                                        25

<210> SEQ ID NO 14
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
cgcgcagggt gcagcatgtt tggc                                         24

<210> SEQ ID NO 15
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
gggccttgca ggtgcttcag gtgtc                                        25

<210> SEQ ID NO 16
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
ccgctgttct tggtattaca gagcc                                        25

<210> SEQ ID NO 17
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
gcagcgtcag cgatgccatg tttgc                                        25

<210> SEQ ID NO 18
<211> LENGTH: 25
```

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
gcttggctca ggtgttgcga tcgtc                                    25

<210> SEQ ID NO 19
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
gtacatattg tcgttagaac gcggtaatac gactca                        36

<210> SEQ ID NO 20
<211> LENGTH: 35
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
cgttagaacg cgtaatacga ctcactatag ggaga                         35

<210> SEQ ID NO 21
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
cgctactgct gaacgaacat gtcc                                     24
```

DNA ENCODING SUCROSE PTS ENZYME II

TECHNICAL FIELD

The present invention relates to a DNA encoding sucrose PTS enzyme II, which is a protein involved in uptake of sucrose into a cell of coryneform bacterium.

BACKGROUND ART

Bacteria can assimilate many carbon sources, and various specific systems exist for their cellular transmembrane transport. Moreover, most of bacteria can respond to environmental changes to survive under a limited nutritious condition. Their cells are provided with a detector for monitoring the environment to select their nutrition from various carbon sources. Examples of such transmembrane transport systems and detectors of sugars include PTS (phosphoenolpyruvate/carbohydrate phosphotransferase system or phosphoenolpyruvate-sugar transport system; as for PTS, refer to *Escherichia coli* and *Salmonella* Cellular and Molecular Biology, Second Edition, ASM (American Society for Microbiology) Press).

PTS is involved in regulation of transmembrane transport and phosphorylation of various sugars (PTS sugars), movement towards these carbon sources and many metabolic pathways. PTS catalyzes the following reaction. PEP refers to phosphoenolpyruvic acid.

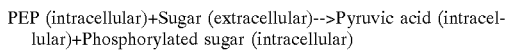

PEP (intracellular)+Sugar (extracellular)-->Pyruvic acid (intracellular)+Phosphorylated sugar (intracellular)

PTS catalyzes a reaction for generating a phosphorylated sugar and pyruvic acid by translocating a phosphate group of intracellular phosphoenolpyruvic acid (also referred to as "PEP" hereafter) to an extracellular sugar. The phosphorylation of a sugar is linked with cellular transmembrane transport of a sugar, and energies required for these processes are supplied from PEP, which is an intermediate of the glycolytic pathway.

In *Escherichia coli* and *Salmonella typhimurium*, proteins constituting PTS catalyze the following reactions.

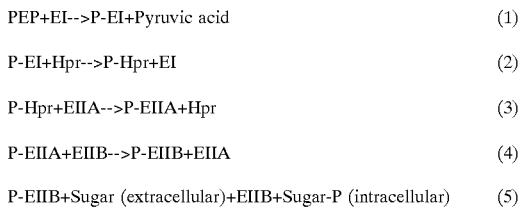

| PEP+EI-->P-EI+Pyruvic acid | (1) |
| P-EI+Hpr-->P-Hpr+EI | (2) |
| P-Hpr+EIIA-->P-EIIA+Hpr | (3) |
| P-EIIA+EIIB-->P-EIIB+EIIA | (4) |
| P-EIIB+Sugar (extracellular)+EIIB+Sugar-P (intracellular) | (5) |

Among proteins involved in the above reactions, EI (Enzyme I) and Hpr (histidine protein) are soluble cytoplasmic proteins involved in phosphorylation of all PTS sugars and referred to as general PTS proteins.

On the other hand, EII (Enzyme II) is specific for PTS sugars and consists of several domains or proteins depending on the sugars. For example, the mannitol-specific EII is a membrane-bound protein consisting of three domains, A, B and C. The glucose-specific EII and sucrose-specific EII consist of IIB and IIC, which are membrane-bound proteins, and IIA, which is a soluble protein. In any case, translocation of a phosphate group from PEP to a sugar is mediated by EI, HPr, EIIA and EIIB. The EIIC domain, which is an intramembranous portion of EII, forms a translocation channel and is considered to be probably a specific binding site of a substrate.

The third type of EII is observed in mannose PTS. Both of its domains A and B are fused in a single soluble polypeptide, and the two intramembranous proteins (IIC and IID) are involved in transmembrane transport of mannose.

In *Escherichia coli* and *Salmonella typhimurium*, the gene encoding EI (ptsI) has been cloned and sequenced (Saffen, E. W. et al., *J. Biol. Chem.*, 262, pp.16241–16253, 1987: De Reuse, H. and Danchin, A., *J. Bacteriol.*, 170, pp.3827–3837, 1988). Further, EII specific for some sugars have also been cloned (Saffen, E. W. et al., *J. Biol. Chem.*, 262, pp.16241–16253, 1987; Erni, B. and Zanolari, B., *J. Biol. Chem.*, 261, pp.16398–16403, 1986; Nelson, S. O. et al., *EMBO J.*, 3, pp.1587–1593, 1984).

It is known that some kinds of sugars are taken up by non-PTS, which do not require PEP, as a system for uptake into cells.

DISCLOSURE OF THE INVENTION

As described above, many studies about uptake of sugar into cells have been performed, but studies about PTS in industrially useful coryneform bacteria have not made much progress. Accordingly, an object of the present invention is to provide a gene encoding a protein constituting sucrose PTS in coryneform bacterium.

The inventors of the present application isolated a DNA fragment including a gene encoding sucrase (invertase) of coryneform bacterium and determined its structure. Further, they developed a method for producing an amino acid or a nucleic acid by using a coryneform bacterium containing the amplified sucrase gene (Japanese Patent Laid-open Publication (Kokai) Nos. 5-244958 and 8-196280). In the DNA fragment, four open reading frames (ORF-F1, ORF-F2, ORF-F3 and ORF-F4) exist in a SmaI fragment of about 6 kb.

However, the inventors of the present invention considered based on comparison with other sucrase genes that the aforementioned ORF-F2 did not contain the sucrase gene in full length. That is, the number of amino acid residues in sucrase estimated from known sucrase genes is 466 to 511 (Gunaseakren, P., *J. Bacteriol.*, 172 (12), pp.6727–35, 1990), whereas the amino acid sequence that can be encoded by ORF-F2 contains 424 amino acid residues, which was relatively short. Therefore, a sequence existing downstream from ORF-F2 was cloned again and its nucleotide sequence was determined. As a result, it was revealed that the DNA fragment containing the aforementioned sucrase gene consisted of two independent cloned fragments ligated to each other, and it was found that a novel gene encoding sucrose PTS enzyme II existed downstream from the sucrase gene. Thus, the present invention was accomplished.

That is, the present invention provides a protein defined in the following (A) or (B):

(A) a protein which has the amino acid sequence of SEQ ID NO: 2 in Sequence Listing;

(B) a protein which has the amino acid sequence of SEQ ID NO: 2 in Sequence Listing including substitution, deletion, insertion, addition or inversion of one or several amino acids, and an activity for binding to sucrose.

The present invention also provides a DNA which encodes a protein defined in the following (A) or (B):

(A) a protein which has the amino acid sequence of SEQ ID NO: 2 in Sequence Listing;

(B) a protein which has the amino acid sequence of SEQ ID NO: 2 in Sequence Listing including substitution, deletion, insertion, addition or inversion of one or several amino acids, and an activity for binding to sucrose.

The aforementioned DNA includes a DNA defined in the following (a) or (b):

(a) a DNA which contains the nucleotide sequence of the nucleotides 3779 to 5761 of SEQ ID NO: 1 in Sequence Listing;

(b) a DNA which is hybridizable with a nucleotide sequence containing the nucleotide sequence of the nucleotides 3779 to 5761 of SEQ ID NO: 1 in Sequence Listing under a stringent condition, and encodes a protein having an activity for binding to sucrose.

BEST MODE FOR CARRYING OUT THE INVENTION

Figure 1:
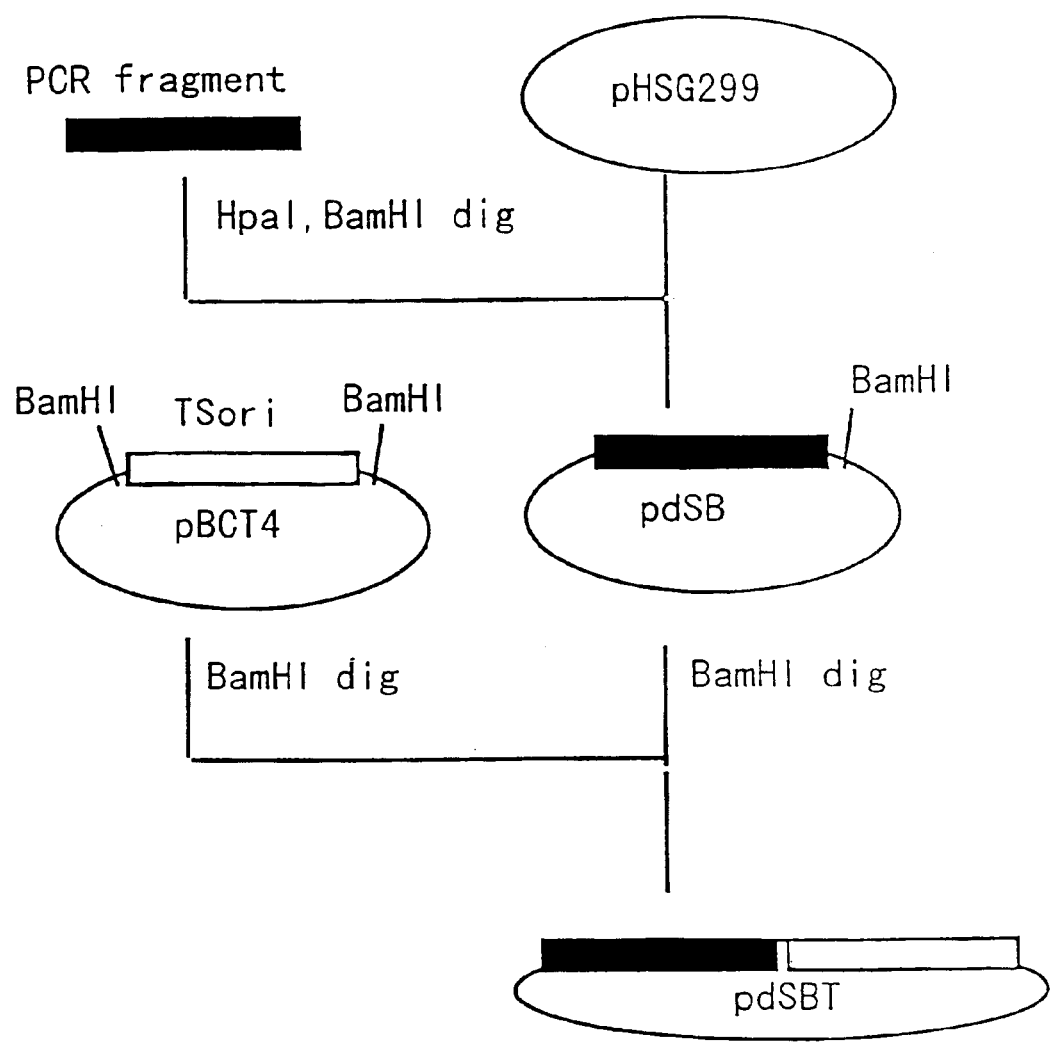
FIG. 1 shows a construction process of a plasmid for disrupting the sucrose PTS enzyme II gene.

Hereafter, the present invention will be explained in detail.

The DNA of the present invention was obtained, in the examples described later, by amplifying a region existing downstream from the sucrase gene on chromosomal DNA of *Brevibacterium lactofermentum* by PCR (polymerase chain reaction).

A region adjacent to a known region on a chromosomal DNA can be amplified by ligating a cassette to a DNA fragment containing the regions and performing PCR using a primer corresponding to the known region and a primer corresponding to the cassette. At this time, if the 5' end of the cassette is dephosphorylated beforehand, a nick is generated at a ligation site of the chromosomal DNA fragment and 5' end of the cassette. Therefore, DNA synthesis started from the cassette primer will be stopped at this ligation site, and only the DNA synthesized from a synthetic primer will serves as a template for synthesis starting from the cassette primer and a complementary chain will be formed. As a result, specific amplification becomes possible (cassette-ligation mediated PCR method (*Molecular and Cellular Probes*, 6, pp.467–475)). A kit utilizing this method is commercially available (TAKARA LA PCR™ in vitro Cloning Kit, Takara Shuzo) and can be utilized to obtain the DNA of the present invention.

Since the nucleotide sequences of the DNA of the present invention and the adjacent region thereof have been revealed, they can be directly amplified by PCR using oligonucleotides synthesized based on these nucleotide sequences as primers and chromosomal DNA of coryneform bacterium as a template. Examples of such primers include oligonucleotides having the nucleotide sequences of SEQ ID NOS: 10 and 21. Further, the DNA of the present invention can also be isolated from a chromosomal DNA library by hybridization using an oligonucleotide synthesized based on these nucleotide sequences as a probe. The chromosomal DNA of coryneform bacterium can be obtained by, for example, the method of Saito et al. (described in *Biochim. Biophys. Acta*, 72, pp.619–629, 1963) or the method of K. S. Kirby (*Biochem. J.*, 64, p.405, 1956).

Further, conventional methods well known to those skilled in the art can be employed for preparation of chromosomal DNA, preparation of chromosomal DNA library, hybridization, PCR, preparation of plasmid DNA, digestion and ligation of DNA, transformation, design of oligonucleotides used as primers and so forth. These methods are described in Sambrook, J., Fritsch, E. F., and Maniatis, T., "Molecular Cloning A Laboratory Manual, Second Edition", Cold Spring Harbor Laboratory Press, 1989 and so forth.

Plasmids used for cloning of the DNA of the present invention, preparation of a chromosomal DNA library or the like may be those that can replicate in microorganisms such as bacteria belonging to the genus *Escherichia*, and specific examples thereof include pBR322, pTWV228, pMW119, pUC19 and so forth.

An example of the nucleotide sequence of a DNA fragment containing the DNA of the present invention obtained as described above is shown as SEQ ID NO: 1 in Sequence Listing. The region containing the nucleotide sequence of the nucleotides 3779 to 5761 in this nucleotide sequence encodes sucrose PTS enzyme II, which is the protein of the present invention. In the nucleotide sequence of SEQ ID NO: 1, the nucleotides 342 to 1505 and the nucleotides 2338 to 3609 correspond to ORF-F1 and ORF-F2, respectively, in the DNA fragment containing the sucrase gene described in Japanese Patent Laid-open Publication (Kokai) No. 8-196280. Further, when the nucleotide sequence of SEQ ID NO: 1 and the nucleotide sequence described in Japanese Patent Laid-open Publication (Kokai) No. 8-196280 are compared, a region of the nucleotides 1 to 3687 in the nucleotide sequence of SEQ ID NO: 1 was identical to the nucleotide sequence described in Japanese Patent Laid-open Publication (Kokai) No. 8-196280. Accordingly, it was revealed that the DNA fragment containing the sucrase gene consisted of two independent cloned fragments.

The DNA of the present invention may be a DNA that encodes sucrose PTS enzyme II including substitution, deletion, insertion, addition or inversion of one or several amino acids at one or a plurality of sites so long as the activity for binding to sucrose of the encoded sucrose PTS enzyme II is not deteriorated. The number meant by the term "several" used herein may vary depending on locations of amino acid residues in the three-dimensional structure of proteins and kinds of amino acid residues. This is due to the fact that there are highly analogous amino acids among amino acids such as isoleucine and valine, and difference among such amino acids does not substantially affect the three-dimensional structure of proteins. Therefore, the protein may be one having homology of 70% to 80% or higher, preferably, 90% to 95%, with respect to the whole amino acid sequence constituting sucrose PTS enzyme II and having an activity for binding to sucrose. Specifically, the term "several" means 2 to 180, preferably 2 to 60, more preferably 2 to 5.

Such a DNA encoding a protein which is substantially identical to sucrose PTS enzyme II as mentioned above can be obtained by modifying a nucleotide sequence so that the amino acid sequence at a particular site should include substitution, deletion, insertion, addition or inversion of an amino acid residue or residues through, for example, site-specific mutagenesis. Further, such a modified DNA as mentioned above may also be obtained by a conventional mutagenesis treatment. Examples of the mutagenesis treatment include an in vitro treatment of DNA encoding sucrose PTS enzyme II with hydroxylamine or the like, a treatment of microorganisms such as *Escherichia* bacteria containing the DNA encoding sucrose PTS enzyme II by UV irradiation or with mutagenesis agents used for a usual mutagenesis treatment such as N-methyl-N'-nitro-N-nitrosoguanidine (NTG) and nitrous acid.

The aforementioned substitution, deletion, insertion, addition, inversion or the like of nucleotides includes naturally occurring mutations (mutant or variant) such as those observed depending on differences of strains, species or genera of microorganisms containing sucrose PTS enzyme II and so forth.

A DNA which encodes a protein substantially the same as sucrose PTS enzyme II can be obtained by, for example, isolating a DNA which is hybridizable with a DNA having the nucleotide sequence of the nucleotides 3779 to 5761 of the nucleotide sequence of SEQ ID NO: 1 in Sequence Listing or a probe prepared from DNA having the nucleotide sequence by PCR or the like under stringent conditions and encoding a protein containing sucrose PTS enzyme II having an activity for binding to sucrose from DNA encoding sucrose PTS enzyme II containing a mutation or a cell containing it. The "stringent conditions" referred to herein is a condition under which a so-called specific hybrid is formed, but a non-specific hybrid is not formed. It is difficult to clearly define this condition by using numerical values. However, for example, the stringent conditions include a condition under which two of DNAs having high homology, for example, two of DNAs having homology of not less than 50% are hybridized with each other, but two of DNAs having homology lower than the above level are not hybridized with each other. Alternatively, the stringent conditions are exemplified by a hybridization condition represented by salt concentrations of 1×SSC. 0.1% SDS, preferably 0.1× SSC, 0.1% SDS, at 60° C., which is an ordinary condition of washing in Southern hybridization. The homology used herein is represented with a value calculated by the method of Lipman-Pearson (Science, 227, pp.1435–1441, 1985) or the method of Takashi & Gotoh (J. Biochem., 92, pp.1173–1177, 1984). The probe can be designed according to a method known to those skilled in the art.

Those genes hybridizable under the condition as described above include those having a stop codon generated in the genes, but such genes can be easily removed by ligating them to a commercially available expression vector to examine size of the expressed product.

The protein of the present invention is a protein encoded by the DNA of the present invention and has the amino acid sequence of SEQ ID NO: 2. The protein of the present invention may have an amino acid sequence corresponding to the amino acid sequence of SEQ ID NO: 2 in Sequence Listing including substitution, deletion, insertion, addition or inversion of one or several amino acids so long as it has an activity for binding to sucrose.

The DNA of the present invention can be utilized to improve sucrose uptake ability of coryneform bacteria or the like. Further, since PTS consumes PEP for uptake of a sugar into a cell, PTS is considered to be disadvantageous for synthesis of amino acids of which biosynthesis system include PEP in an upstream stage. Therefore, if sucrose PTS is disrupted and sucrose can be taken up by an uptake system which does not require PEP, it is considered advantageous in view of sucrose uptake rate or productivity of an amino acid or the like. In coryneform bacteria, non-PTS specific for sucrose is not known, but, for example, if sucrase is allowed to act extracellularly, glucose and fructose can be taken up by non-PTS.

Further, if the DNA of the present invention is modified so as to encode sucrose PTS enzyme II having an enhanced or suppressed function or so as to be ligated to an expression control sequence such as a promoter derived from other genes and introduced into a coryneform bacterium, a coryneform bacterium having an enhanced or suppressed sucrose uptake ability can be created. Specifically, a DNA encoding sucrose PTS enzyme II having an enhanced function is introduced into an autonomously replicable vector or chromosomal DNA in a cell of coryneform bacterium. Further, a DNA encoding sucrose PTS enzyme II having a suppressed function is introduced into chromosomal DNA by gene substitution utilizing homologous recombination. Alternatively, a coryneform bacterium in which sucrose PTS functions at low temperature but does not function at high temperature can be created by gene substitution using a plasmid containing a temperature sensitive replication control region (see Japanese Patent Publication (Kokoku) No. 7-108228).

Coryneform bacteria to which the present invention is applicable include those bacteria having been hitherto classified into the genus *Brevibacterium* but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform bacteria are mentioned below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes* (*Corynebacterium ammoniagenes*)
*Brevibacterium album*
*Brevibacterium cerium*
*Microbacterium ammoniaphilum*

Examples of the vector autonomously replicable in a cell of coryneform bacterium include pAM330 (refer to Japanese Patent Laid-open (Kokai) No. 58-67699), pHM1519 (refer to Japanese Patent Laid-open (Kokai) No. 58-77895) and so forth. Moreover, if a DNA fragment having an ability to make a plasmid autonomously replicable in coryneform bacterium is excised from these vectors and inserted into the vectors for *Escherichia coli*, they can be used as a so-called shuttle vector autonomously replicable in both of *Escherichia coli* and coryneform bacteria. Examples of such a shuttle vector include those mentioned below. There are also indicated microorganisms that harbor each vector, and accession numbers thereof at international depositories are shown in the parentheses, respectively. Among these, pHSC4 includes a temperature sensitive replication control region.

pAJ655 *Escherichia coli* AJ11882 (FERM BP-136) *Corynebacterium glutamicum* SR8201 (ATCC39135)
pAJ1844 *Escherichia coli* AJ11883 (FERM BP-137) *Corynebacterium glutamicum* SR8202 (ATCC39136)
pAJ611 *Escherichia coli* AJ11884 (FERM BP-138)

pAJ3148 *Corynebacterium glutamicum* SR8203 (ATCC39137)
pAJ440 *Bacillus subtilis* AJ11901 (FERM BP-140)
pHC4 *Escherichia coli* AJ12617 (FERM BP-3532)
pHSC4 *Escherichia coli* AJ12571 (FERM BP-3524)

A recombinant vector containing the DNA of the present invention can be introduced into a coryneform bacterium according to a transformation method reported so far. For instance, there are a method of treating recipient cells with calcium chloride so as to increase the permeability of DNA, which has been reported for *Escherichia coli* K-12 (Mandel, M. and Higa, A., *J. Mol. Biol.*, 53, 159, 1970); and a method of preparing competent cells from cells which are at the growth phase followed by introducing the DNA thereinto, which has been reported for *Bacillus subtilis* (Duncan, C. H., Wilson, G. A. and Young, F. E., *Gene*, 1, 153, 1977). In addition to these, also employable are a method of making DNA-recipient cells into protoplasts or spheroplasts, which can easily take up recombinant DNA, followed by introducing the recombinant DNA into the DNA-recipient cells, which method is known to be applicable to *Bacillus subtilis*, actinomycetes and yeasts (Chang, S. and Choen, S. N., *Molec. Gen. Genet.*, 168, 111, 1979; Bibb, M. J., Ward, J. M. and Hopwood, O. A., *Nature*, 274, 398, 1978; Hinnen, A., Hicks, J. B. and Fink, G. R., *Proc. Natl. Acad. Sci., USA*, 75, 1929, 1978) and the electric pulse method (see Japanese Patent Laid-open Publication (Kokai) No. 2-207791).

EXAMPLES

Hereafter, examples of the present invention will be explained in detail.

Example 1

Isolation of Gene Encoding Sucrose PTS Enzyme II

<1>Analysis of Chromosomal DNA of *Brevibacterium lactofermentum* AJ12036 (FERM BP-734) by Southern Hybridization The Brevibacterium lactofermentumAJ12036 strain was cultured overnight in 4 ml of M-CM2S medium (containing 5 g/L of sucrose, 10 g/L of polypeptone, 10 g/L of yeast extract, 5 g/L of NaCl and 0.1 g/L of DL-methionine) and microbial cells were collected. Chromosomal DNA was extracted from the obtained microbial cells by using a Bacterial Geneomic DNA Purification Kit (Advanced Genetic Technologies). The chromosomal DNA was eluted with 50 µl of TE buffer (composition: 10 mM tris-HCl (pH 7.5), 1 mM EDTA-2Na).

The chromosomal DNA extracted as described above was subjected to Southern hybridization according to the method described in Molecular Cloning, A Laboratory Manual, Second Edition, Cold Spring Harbor Laboratory Press, 1989. The chromosomal DNA was separately digested with BamHI and SmaI, which did not cleave regions on the C-terminus side of ORF-F2 and N-terminus side of ORF-F3 and subjected to agarose gel electrophoresis. As a probe, a fragment of about 3 kb was used that was excised from 6.9 kb fragment cloned on pSSM30 (Japanese Patent Laid-open Publication (Kokai) No. 8-196280) with BamHI to cover the regions on the C-terminus side of ORF-F2 and on the N-terminus side of ORF-F3 (Japanese Patent Laid-open Publication (Kokai) No. 8-196280, the fragment of SEQ ID NO: 1649 to 4675 in Sequence Listing).

As a result of the hybridization, two bands were detected, and it was revealed that ORF-F2 and ORF-F3 were not adjacent to each other on the chromosome. Therefore, it was attempted to confirm a sequence existing downstream from the sucrase gene again.

<2>Determination of Sequence of Region Existing Downstream from Sucrase Gene

To determine the nucleotide sequence of a region downstream from the sucrase gene, the downstream region was first amplified by PCR. PCR was performed by using a TAKARA LA PCR™ in vitro Cloning Kit (Takara Shuzo). Specifically, the PCR was performed as follows.

The chromosomal DNA was completely digested with 10 kinds of restriction enzymes (SpeI, EcoT14I, NheI, PstI, EcoT22I, BglII, BamHI, XhoI, SalI, AvaI), which produced the same cleavage ends as cassettes (SEQ ID NOS: 3 to 8 in Sequence Listing) attached to the aforementioned kit. PCR was performed by using each of these fragments as a template, Synthetic primer 1 shown in Table 1 and Cassette primer 1 (SEQ ID NO: 19). Since a phosphate group was not added to the 5' end of the cassette, a nick was generated at the ligation site of the chromosomal DNA fragment and the 5' end of the cassette. Therefore, the DNA synthesis starting from the cassette primer stopped at this ligation site, and only the DNA synthesized from the synthetic primer served as a template for synthesis starting from the cassette primer, and a complementary chain was formed.

Subsequently, PCR was performed out by using the amplification product obtained above as a template, Synthetic primer 2 and Cassette primer 2 (SEQ ID NO: 20). As a result, a fragment could be amplified when a DNA obtained by digesting the chromosomal DNA with EcoT14I, PstI, BglII, BamHI, XhoI or AvaI was used as a template. The nucleotide sequence of a fragment of about 1.8 kb amplified by using the DNA fragment digested with BamHI as a template was determined.

TABLE 1

Nucleotide sequence and position of synthetic primer

| Primer Number | Nucleotide sequence | Location in SEQ ID NO: 1 (nucleotide number) |
|---|---|---|
| 1 | CGTCTTGCGAGGATTCAGCGAGCTG (SEQ ID NO: 9) | (3159 to 3183) |
| 2 | AGCTGGATTTCGGCCATGAATTCTA (SEQ ID NO: 10) | (3179 to 3203) |
| 3 | GATCTGTTCGGTCCGCAATCACT (SEQ ID NO: 11) | (4189 to 4212) |
| 4 | CACTGGTGGAGATGTTCCCTCAGAT (SEQ ID NO: 12) | (4209 to 4233) |
| 5 | CATCTTCGCAACCGCATCCATGGCC (SEQ ID NO: 13) | (4801 to 4825) |
| 6 | CGCGCAGGGTGCAGCATGTTTGGC (SEQ ID NO: 14) | (4831 to 4854) |
| 7 | GGGCCTTGCAGGTGCTTCAGGTGTC (SEQ ID NO: 15) | (4888 to 4912) |
| 8 | CCGCTGTTCTTGGTATTACAGAGCC (SEQ ID NO: 16) | (4914 to 4938) |
| 9 | GCAGCGTCAGCGATGCCATGTTTGC (SEQ ID NO: 17) | (5322 to 5346) |
| 10 | GCTTGGCTCAGGTGTTGCGATCGTC (SEQ ID NO: 18) | (5356 to 5380) |

Synthetic primers 3 and 4 were synthesized based on the determined sequences. In the same manner as described above, the fragments were successively amplified by PCR using a combination of Synthetic primer 3 and Cassette primer 1 and a combination of Synthetic primer 4 and Cassette primer 2. As a result, a fragment could be amplified when a DNA obtained by digesting the chromosomal DNA with PstI or BamHI was used as a template. The nucleotide sequence of the fragment amplified based on the DNA fragment digested with PstI was determined.

Synthetic primers 5 and 6 were synthesized based on the determined sequence. PCR was successively carried out by using a combination of Synthetic primer 5 and Cassette primer 1 and a combination of Synthetic primer 6 and Cassette primer 2. As a result, an amplified fragment could be confirmed when the chromosomal DNA digested with EcoT14 or PstI was used as a template. The nucleotide sequence of the fragment of the former case was determined.

Further, Synthetic primers 7 and a were synthesized and the same procedure as described above was performed. As a result, an amplified fragment could be confirmed when EcoT14-digested chromosomal DNA was used as a template. The nucleotide sequence of this amplified fragment was determined.

Primers 9 and 10 were synthesized based on the above sequence, and the same procedure as described above was performed. As a result, an amplified fragment could be confirmed when SpeI-digested chromosomal DNA was used as a template. The nucleotide sequence of this amplified fragment was determined.

As for the nucleotide sequence determination, a reaction was performed by using a sequencing kit produced by ABI according to its protocol, and then the nucleotide sequence of the amplified fragment was determined by the fluorescence labeling method.

The above results are shown in SEQ ID NO: 1 in Sequence Listing. It was found that a novel ORF existed after the nucleotide number 3684 in this nucleotide sequence. It was inferred that this ORF consisted of the nucleotide sequence of 1983 bp corresponding to the nucleotide numbers 3779 to 5761, and that a protein obtained by translating the determined nucleotide sequence consisted of 661 amino acids. As for the ORF, homology search was performed in the GENBANK CDS database. As a result, as shown in Table 2, the proteins that could be encoded by the ORF showed high homology with sucrose PTS enzyme II, a protein specific for sucrose uptake. Hereafter, this ORF is referred to as ptsIIsuc gene.

TABLE 2

Results of homology search of novel ORF

| Name of Bacterium and gene | Known protein showing homology | Homology (%) |
|---|---|---|
| P. pantsaceus | scrA | Enzyme IIscr | 48.8 |
| B. subtilis | treP | Trehalose-specific enzyme IIBC | 43.4 |
| S. xylosus | scrA | Enzyme IIscr | 52.2 |
| S. mutans | scrA | Enzyme IIscr | 45.4 |
| S. typhimurium plasmid pUR400 | scrA | Enzyme Iiscr | 37.6 |

Example 2

Preparation of Sucrose PTS Enzyme II Gene-disrupted Strain

A Brevibacterium lactofermentum strain with a disrupted ptsIIsuc gene was prepared. First of all, a plasmid for disrupting the gene was prepared (FIG. 1). A ptsIIsuc gene fragment amplified by PCR using the chromosome of Brevibacterium lactofermentum AJ12036 as a template, Primer 2 (SEQ ID NO: 10) and Primer 11 (SEQ ID NO: 21) having the nucleotide sequence shown below was cloned by using a TA cloning kit (Invitrogen), and the plasmid was designated as pCRS2.
(Primer 11)
CGCTACTGCTGAACGAACATGTCC (corresponding to the nucleotide numbers 5947 to 5924 in SEQ ID NO: 1)

A fragment excised from pCRS2 by digestion with XbaI and SpeI was ligated to the XbaI ends of pHSG399 to construct p399S2. This plasmid was digested with HpaI and BamHI, and the obtained fragment (corresponding to the nucleotide numbers 4385 to 4798 in SEQ ID NO: 1) was ligated to pHSG299 digested with SmaI and BamHI to prepare a plasmid pdSB. Subsequently, pdSB was digested with BamHI and ligated to a temperature sensitive replication origin that was excised from plasmid pBCT4 by digestion with BamHI and could replicate in coryneform bacteria (refer to Japanese Patent Publication (Kokoku) No. 7-108228) to prepare a plasmid pdSBT. The plasmid included the ptsIIsuc gene having deleted 5' end and 3' ends. The pdSBT could autonomously replicate in coryneform bacteria at about 10° C. to 32° C., but not at about 34° C. or higher.

Figure 2:
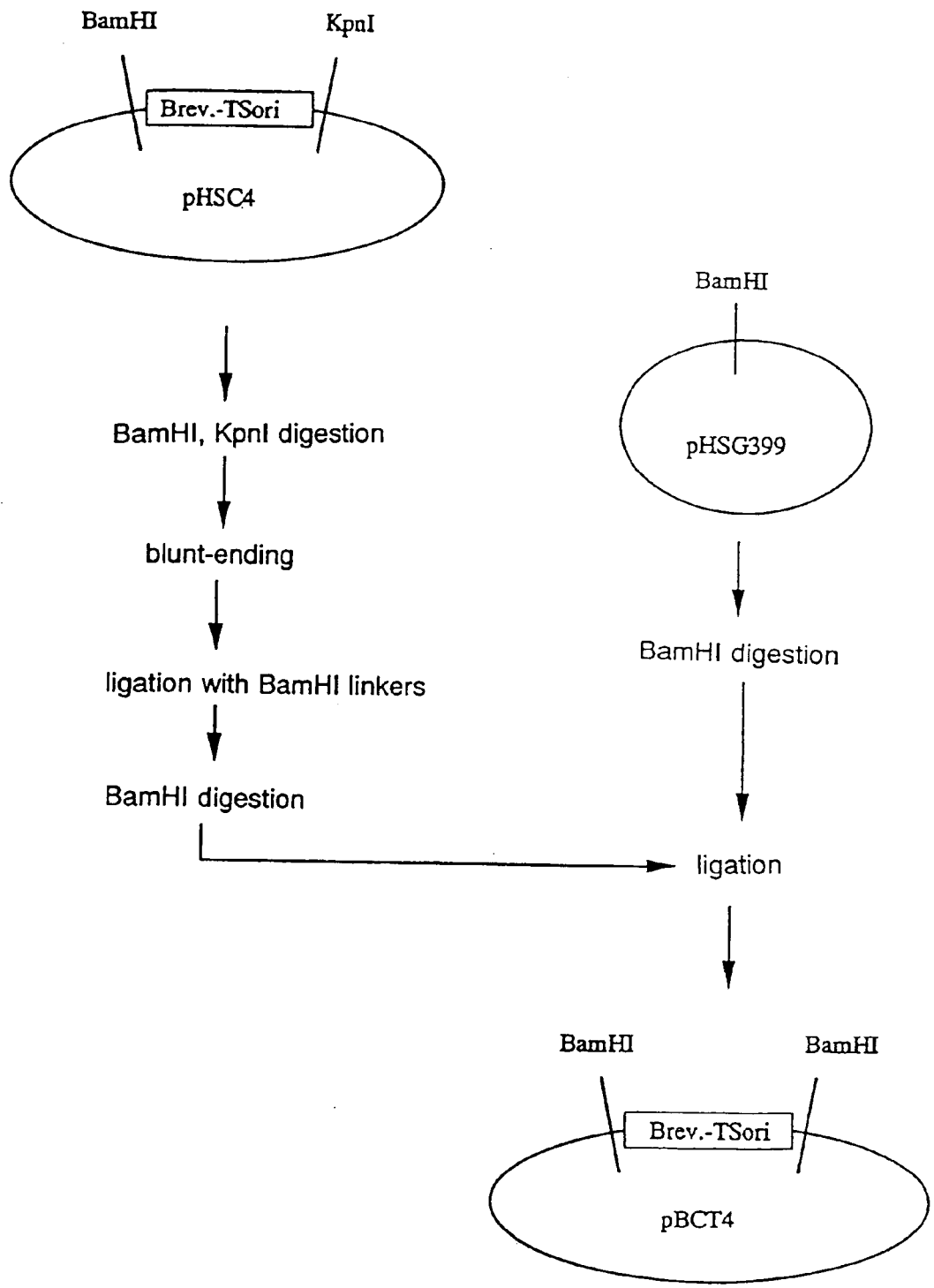
FIG. 2 shows a construction process of pBCT4.

The pBCT4 was constructed as follows. A temperature sensitive vector pHSC4 described in Japanese Patent Publication (Kokoku) No. 7-108228 was digested with restriction enzymes, BamHI and KpnI, to obtain a DNA fragment of about 3 kb containing the obtained temperature sensitive replication origin. Both of the ends of the obtained DNA fragment were blunt-ended with T4 DNA polymerase. This DNA fragment was ligated with BamHI linkers and digested with BamHI again. Then, it was ligated to pHSG399 digested with BamHI to obtain pBCT4 (FIG. 2).

The Brevibacterium lactofermentum AJ12036 strain was transformed with pdSBT and a transformant was selected by using a CM2S plate containing 25 µg/ml of kanamycin. The transformation was performed by the electric pulse method (refer to Japanese Patent Laid-pen Publication (Kokai) No. 2-207791). The obtained transformant was designated as AJ12036/pTSBT. The AJ12036/pTSBT strain was diluted and spread on M-CM2S plates containing 25 µg/ml of kanamycin at $10^3$ to $10^5$ cfu per plate. The transformants on the plates were cultured overnight at 34° C., and a strain showing drug resistance was obtained as a strain containing the plasmid incorporated into its chromosome. It was confirmed by PCR that the obtained strain had the vector plasmid incorporated into the pTSIIsuc gene of the host chromosome by homologous recombination. This integrated strain was designated as YdS1.

The YdS1 strain was cultured at 34° C. in a minimal medium containing glucose or sucrose as a sugar source (20 g/L of glucose or sucrose, 5 g/L of ammonium sulfate, 2 g/L of urea, 1 g/L of $KH_2PO_4$, 0.5 g/L of $MgSO_4 \cdot 7H_2O$, 0.002 g/dl of $FeSO_4$, 0.002 g/dl of $MnSO_4$, 100 µg/L of biotin, 2000 µg/L of vitamin B1, 10 mg/dl of DL-methionine and 15 g/L of agar, pH 6.6). The results are shown in Table 3. Since the YdS1 strain could grow in the minimal medium containing only glucose as a carbon source, but not in the minimal medium containing only sucrose as a carbon source, it was confirmed that the ptsIIsuc gene is the gene encoding Enzyme II which is a protein specific for sucrose in sucrose uptake.

TABLE 3

| | Growth on minimal medium | |
|---|---|---|
| Bacterial | Carbon source | |
| strain | Sucrose | Glucose |
| AJ12036 | Possible to grow | Possible to grow |
| YdS1 | Impossible to grow | Possible to grow |

INDUSTRIAL APPLICABILITY

The present invention provides a gene encoding sucrose PTS enzyme II of coryneform bacterium and a strain of coryneform bacterium in which sucrose PTS does not function. These gene and bacterial strain can be utilized in breeding of strains with improved sugar uptake rate or improved productivity of an amino acid, a nucleic acid or the like.

What is claimed is:

1. An isolated protein selected from the group consisting of the amino acid sequence of SEQ ID NO: 2 and a variant of the amino acid sequence of SEQ ID NO: 2 which has homology of 95% or more to the amino acid sequence of SEQ ID NO: 2 and has the activity of sucrose binding enzyme II of the phosphotransferase system from *Brevibacterium lactofermentum*.

2. An isolated DNA which encodes a protein comprising the amino acid sequence of SEQ ID NO: 2.

3. The DNA according to claim 2, which comprises the nucleotide sequence of the nucleotides 3779 to 5761 of SEQ ID NO: 1.

4. An isolated DNA which hybridizes with the nucleotide sequence of the nucleotides 3779 to 5761 of SEQ ID NO: 1 under stringent conditions, and which encodes a protein having the activity of sucrose binding enzyme II of the phosphotransferase system from *Brevibacterium lactofermentum*, wherein the stringent conditions comprise washing at a salt concentration corresponding to 1×SSC, 0.1% SDS, at 60° C.

5. The DNA according to claim 4, wherein the DNA encodes the protein having homology of 95% or more to the amino acid sequence of SEQ ID NO: 2.

* * * * *